United States Patent
Nycz et al.

(10) Patent No.: US 7,427,293 B2
(45) Date of Patent: Sep. 23, 2008

(54) OSTEOCHONDRAL PLUG GRAFT, KIT AND METHOD

(75) Inventors: Jeffrey H Nycz, Collierville, TN (US); Keith M Kinnane, Bartlett, TN (US); Susan J Drapeau, Cordova, TN (US); Daniel A Shimko, Germantown, TN (US); Jeetendra S Bharadwaj, Memphis, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 98 days.

(21) Appl. No.: 11/390,081

(22) Filed: Mar. 28, 2006

(65) Prior Publication Data

US 2007/0233264 A1 Oct. 4, 2007

(51) Int. Cl.
*A61F 2/08* (2006.01)

(52) U.S. Cl. ............... 623/14.12; 623/16.11; 623/18.11; 623/23.57; 623/23.63; 606/99; 606/151

(58) Field of Classification Search .............. 623/23.48, 623/23.61, 23.63, 23.62, 14.12, 23.57
See application file for complete search history.

(56) References Cited

U.S. PATENT DOCUMENTS

| | | | |
|---|---|---|---|
| 5,549,673 A | 8/1996 | Beale | |
| 5,632,745 A | 5/1997 | Schwartz | |
| 5,723,331 A * | 3/1998 | Tubo et al. ................. | 435/366 |
| 5,876,452 A | 3/1999 | Athanasion | |
| 5,921,987 A | 7/1999 | Stone | |
| 6,013,853 A | 1/2000 | Athanasion | |
| 6,146,385 A | 11/2000 | Torrie | |
| 6,270,503 B1 | 8/2001 | Schmeiding | |
| 6,488,033 B1 | 12/2002 | Cerundolo | |
| 6,514,286 B1 | 2/2003 | Leatherbury | |
| 6,530,928 B1 | 3/2003 | Frei | |
| 6,610,067 B2 | 8/2003 | Tallarida | |
| 6,737,072 B1 | 5/2004 | Angele | |
| 6,852,114 B2 | 2/2005 | Cerundolo | |
| 6,869,282 B2 | 3/2005 | Carmichael | |
| 6,872,819 B1 | 3/2005 | Pavesio | |
| 2002/0099446 A1 * | 7/2002 | MacArthur ............... | 623/20.14 |
| 2003/0114937 A1 * | 6/2003 | Leatherbury et al. ...... | 623/23.72 |
| 2003/0216669 A1 * | 11/2003 | Lang et al. ................. | 600/587 |
| 2003/0229400 A1 | 12/2003 | Masuda | |
| 2004/0033212 A1 | 2/2004 | Thomson | |
| 2004/0034419 A1 | 2/2004 | Carter | |
| 2004/0059425 A1 | 3/2004 | Schmieding | |
| 2004/0230303 A1 | 11/2004 | Gomes | |
| 2005/0038520 A1 | 2/2005 | Binette | |

(Continued)

FOREIGN PATENT DOCUMENTS

EP    1561480    8/2005

(Continued)

*Primary Examiner*—Bruce E. Snow
*Assistant Examiner*—Megan Yarnall
(74) *Attorney, Agent, or Firm*—Noreen C. Johnson; Phillip D. Freedman PC; Philip D. Freedman

(57) ABSTRACT

Each of an osteochondral plug graft and a kit comprises a trapezoid shaped construct configured for osteochondral implanting. An osteochondral regeneration method comprises forming a recipient socket in a chondral area of an articular joint in need of repair; harvesting a trapezoid shaped graft from another chondral area; and implanting the trapezoid shaped graft into the recipient socket.

7 Claims, 4 Drawing Sheets

U.S. PATENT DOCUMENTS

| | | |
|---|---|---|
| 2005/0043814 A1* | 2/2005 | Kusanagi et al. .......... 623/23.58 |
| 2005/0064042 A1 | 3/2005 | Vunjak-Bivajivic |
| 2005/0124993 A1 | 6/2005 | Chappuis |
| 2005/0137600 A1 | 6/2005 | Jacobs |
| 2005/0222687 A1 | 10/2005 | Vunjak-Novakovic |
| 2005/0251268 A1 | 11/2005 | Truncala |
| 2006/0020343 A1 | 1/2006 | Ek |
| 2007/0041950 A1* | 2/2007 | Leatherbury et al. ....... 424/93.7 |

FOREIGN PATENT DOCUMENTS

| | | |
|---|---|---|
| EP | 1561481 | 8/2005 |
| EP | 1561438 | 10/2005 |
| WO | WO 03106640 | 12/2003 |

\* cited by examiner

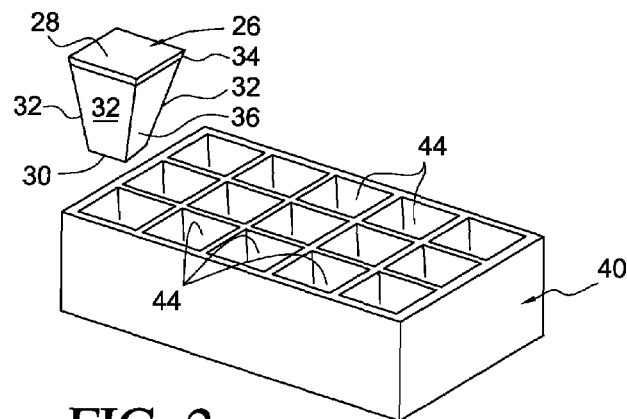
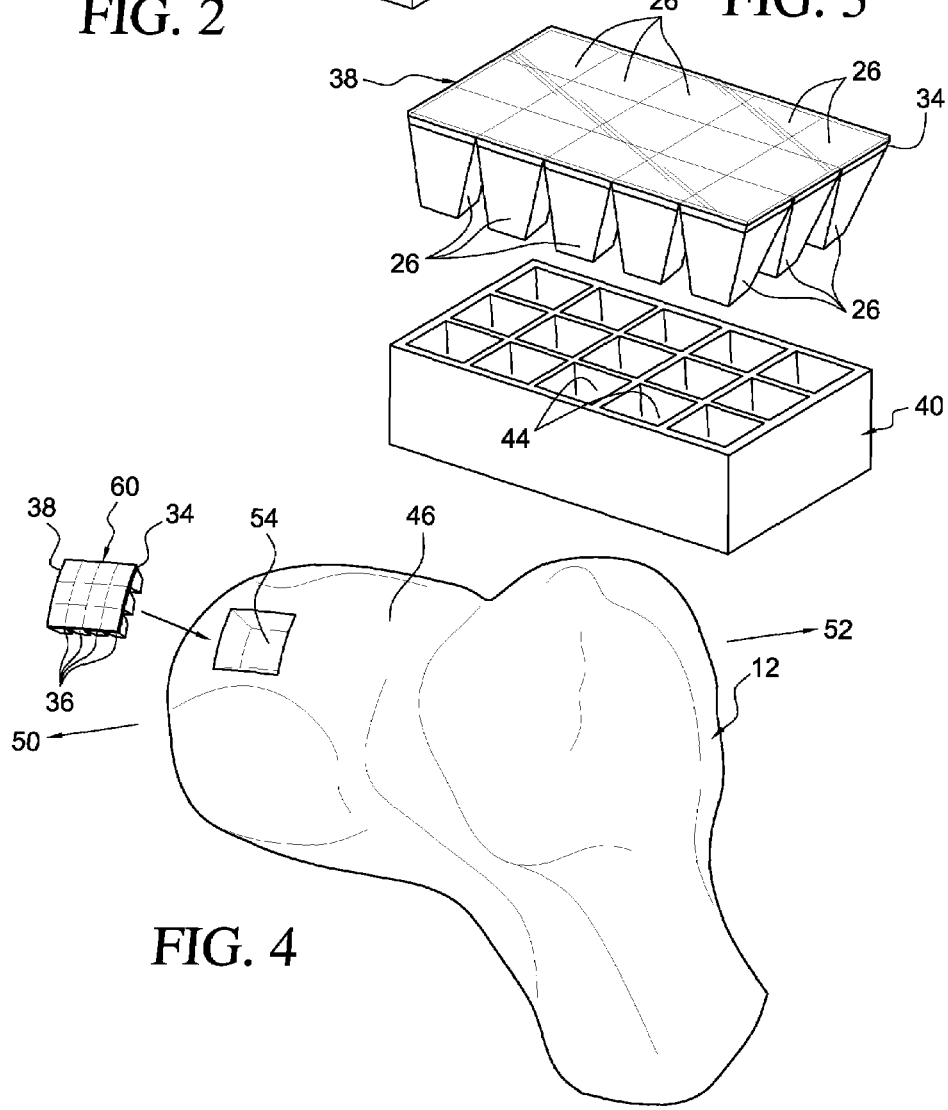

OSTEOCHONDRAL PLUG GRAFT, KIT AND METHOD

BACKGROUND OF THE INVENTION

The invention relates to an osteochondral plug graft, kit for implanting the graft and a method of osteochondral regeneration with the graft.

Human joint surfaces are covered by articular cartilage that provides a resilient, durable surface with low friction. Cartilage is an avascular tissue that has a small number of chondrocytes encapsulated within an extensive extracellular matrix. The cartilage acts to distribute mechanical forces and to protect subchondral bone. The knee is a particular instance of a cartilage surfaced (the condyle) bone area. The knee comprises three bones—the femur, tibia, and patella that are held in place by various ligaments. Corresponding chondral areas of the femur and the tibia form a hinge joint and the patella protects the joint. Portions of the chondral areas as well as the underside of the patella are covered with an articular cartilage that allows the femur and the tibia to smoothly glide against each other without causing damage.

Damage to the articular cartilage, subchondral bone or both can result from traumatic injury or a disease state. For example, articular cartilage in the knee can tear due to traumatic injury as with athletes and degenerative processes as with older patients. The knee cartilage does not heal well due to lack of nerves, blood vessels and a lymphatic system. Hyaline cartilage in particular has a limited capacity for repair and lesions in this material without intervention, can form repair tissue lacking the biomechanical properties of normal cartilage.

A number of procedures are used to treat damaged articular cartilage. Currently, the most widely used procedure involves lavage, arthroscopic debridement and repair stimulation. Repair stimulation is conducted by drilling, abrasion arthroplasty or microfracture. The goal of this procedure is to penetrate into subchondral bone to induce bleeding and fibrin clot formation. This promotes initial repair. However, the resulting formed tissue is often fibrous in nature and lacks the durability of normal cartilage.

Osteochondral grafting has been used to repair chondral damage and to replace damaged articular cartilage and subchondral bone. First in this procedure, cartilage and bone tissue of a defect site are removed by routing to create a bore of a precise cylindrical geometry. Then a cylindrical cartilage and subchondral bone plug graft is harvested in a matching geometry. The harvest is typically from another body region of less strain. The plug graft can be harvested from a recipient source (autograft) or from another suitable human or other animal donor (allograft). The harvested plug graft is then implanted into the bore of the routed defect site. Healing of the graft bone to host bone results in fixation of the plug graft to surrounding host region.

Surface characteristics of the plug graft are critical. For a successful procedure, surface of the transplanted graft must have the same contour as the excised osteochondral tissue. If the contour is not a correct match, a repaired articular surface is at risk for further damage.

Also, osteochondral grafts are typically harvested in a cylindrical plug form. However, a cylindrical shape does not pack well into irregularly shaped defects. Further, cylindrical plug grafts have a propensity to rotate. This results in poor integration of the plug graft with surrounding host tissue.

There is a need for a graft, method and kit to overcome post implantation motion, graft surface mismatch and host tissue integration failure.

BRIEF DESCRIPTION OF THE INVENTION

The invention relates to a trapezoid shaped osteochondral plug graft that fits routed defect shapes, matches adjacent surface contour and resists micromotion after implantation. The osteochondral plug graft comprises a trapezoid shaped construct configured for osteochondral implanting.

In an embodiment, the invention is a method for repairing articular cartilage in a patient, comprising: forming a recipient socket in a chondral area of an articular surface in need of repair; and implanting a trapezoid shaped plug graft into the recipient socket for osteochondral repair of the area.

Another embodiment is a kit for osteochondral regeneration, comprising: a plurality of different configured or different sized trapezoid shaped plug grafts; at least one drill head; and a chisel.

BRIEF DESCRIPTION OF THE DRAWINGS

FIGS. 2 and 3 are schematic perspective views of harvested trapezoid shaped plug grafts and holding array structures;

FIGS. 4 to 6 are schematic perspective views of a femur head;

DETAILED DESCRIPTION OF THE INVENTION

Figure 1:
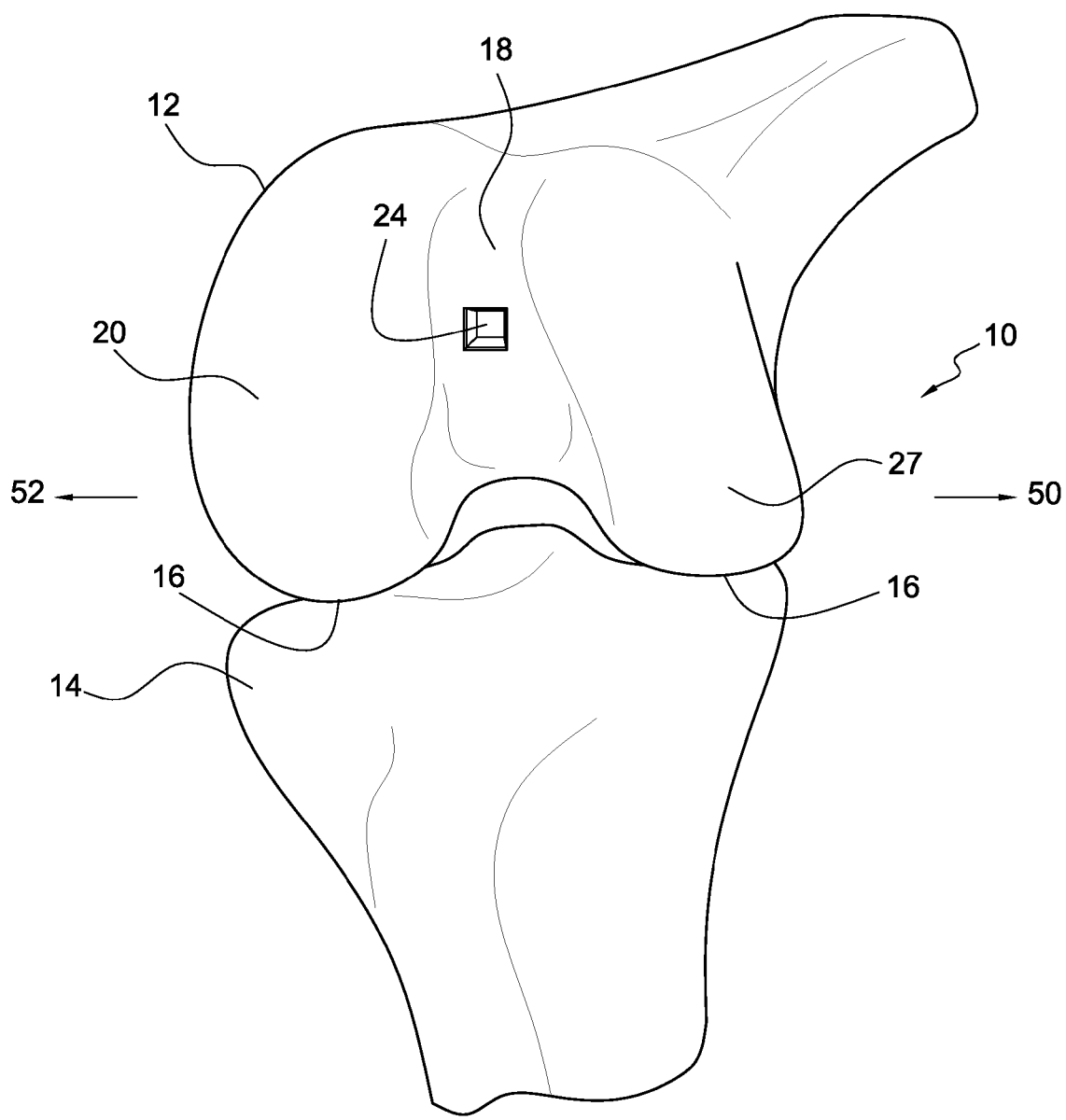
FIG. 1 is a schematic perspective view of a knee joint.

The invention provides a trapezoid shaped plug graft. A "trapezoid" is a quadrilateral having two parallel sides, McGraw-Hill Dictionary of Scientific and Technical Terms, $5^{th}$ Ed., p 2063 (1994). Preferred invention embodiments include a trapezoid shaped plug graft, wherein the trapezoid shape comprises a quadrilateral having only two parallel sides, i.e., four sides are non-parallel and wherein the trapezoid shape comprises a quadrilateral having only four parallel sides, i.e., two sides are non-parallel. At least one cross sectional profile of both these plug graft configurations, tapers from top to bottom surface.

In an embodiment of the invention, an osteochondral plug graft is provided in the form of a trapezoid shaped biphasic construct that has an upper surfaced cartilage area and a subchondral bone lower portion. The trapezoid shaped biphasic construct of the invention is a quadrilateral comprising an articular cartilage top surface with a lower subchondral bone portion having two parallel sides and a bottom surface. The bottom bone surface can be parallel to the articular cartilage top surface. The non parallel subchondral bone sides are tapered from the articular cartilage top surface to permit tight packing of an array of the plug grafts within a routed recipient socket in an osteochondral surface.

This plug graft can be harvested from a recipient or from another suitable human or animal donor and from any appropriate structure including hyaline cartilage and underlying subchondral bone. Suitable harvest locations include joints of mammals, including humans, such as articulating surfaces of knee, hip and shoulder joints. For example, an osteochondral plug can be harvested at the femoral condyle or the articulating surface of a knee joint.

The plug graft can be harvested in any shape and manipulated to provide the trapezoid shape. For example, a cylindrical plug can be reamed from a host osteochondral site and pared into a desired trapezoid shape appropriate for implant into the recipient socket. Or, a plug in a trapezoid shape can be harvested with a punch much like the formation of a square or cube socket with a punch.

An osteochondral plug graft of the invention can have a cross sectional profile that varies along its length. In certain embodiments, the cartilage layer or cap will have a cross sectional profile that is the same as the profile of the underlying bone plug, while in others the cartilage cap will have a cross sectional profile that differs from that of the bone plug. The latter may occur, for instance in grafts having a cartilage cap that extends beyond the periphery of the bone plug or terminates short of the periphery of the bone plug. Similarly, the bone plug itself may have a cross sectional profile that is constant along its length or that varies along its length. Illustrative of the latter point, a cross sectional profile providing a unique, non-circular geometry as discuss herein may occur along only a portion of the bone plug, and yet provide stabilization features as described herein. These and other potential variations will be apparent to the skilled artisan from the descriptions herein.

According to an invention embodiment, a trapezoid shaped allograft osteochondral plug can be either fresh (containing live cells) or processed and frozen or otherwise preserved to remove cells and other potentially antigenic substances while leaving behind a scaffold for patient tissue ingrowth. A variety of such processing techniques is known and can be used in accordance with the invention. For example, harvested osteochondral plugs can be soaked in an agent that facilitates removal of cell and proteoglycan components. One such solution includes an aqueous preparation of hyaluronidase (type IV-s, 3 mg/ml), and trypsin (0.25% in monodibasic buffer 3 ml). The harvested osteochondral plugs can be soaked in this solution for several hours, for example 10 to 24 hours, desirably at an elevated temperature such as 37° C. Optionally, a mixing method such as sonication can be used during the soak. Additional processing steps can include decalcification, washing with water, and immersion in organic solvent solutions such as chloroform/methanol to remove cellular debris and sterilize. After such immersion the grafts can be rinsed thoroughly with water and then frozen and optionally lyophilized. These and other conventional tissue preservation techniques can be applied to the osteochondral grafts in accordance with the present invention.

Osteochondral graft plugs of the invention can be used in the repair of articular cartilage in a patient including for example, cartilage occurring in weight bearing joints such as the knee. The articular cartilage in need of repair can present a full thickness defect, including damage to both the cartilage and the underlying subchondral bone. Such defects can occur from trauma or an advanced stage of disease, including an arthritic disease.

Typically, an articular cartilage site in need of treatment will be surgically prepared for receipt of the osteochondral plug graft. This preparation can include excision of cartilage and subchondral bone at the site to create a socket or void in which the plug graft will be received. Tissue removal can be conducted in any suitable manner including for instance drilling and/or punching, typically in a direction substantially perpendicular to the articular cartilage layer at the site, to create a recipient socket having a depth approximating that of the graft to be implanted. In certain embodiments of the invention as discussed below, the opening for receiving the graft will be created using a drill or punch having a circular cross-section. Multiple, overlapping passes with the drill or punch are made, in order to create an opening having a cross-section defined by multiple, intersecting circular arcs. A chisel can then be used to shape the recipient socket to receive the trapezoid shaped implant.

In another embodiment of the invention, the osteochondral graft is provided as a trapezoid shaped biological matrix supported graft. This graft includes a resorbable osteoconductive matrix, a biological agent such as bone morphogenetic protein (BMP) and optionally, cultured chondrogenic cells. The resorbable osteoconductive matrix can be a biologically acceptable matrix sponge, scaffold, honeycomb, hydrogel, a polymer of an aromatic organic acid or caprolactone suitable for receiving activated migrating chondrocytes or osteocytes that provides a structural support for growth and three-dimensional propagation of chondrocytes and for formulating of new cartilage or for migration of osteochondrocytes into the bone lesions. The support matrix can be prepared from such materials as Type I collagen, Type II collagen, Type IV collagen, fibrin, hyaluronan, alginate, chitosan, gelatin, agarose, cell-contracted collagen containing proteoglycans, glycosaminoglycans or glycoproteins, polymers of aromatic organic acids, fibronectin, laminin, bioactive peptide growth factors, cytokines, elastin, fibrin, synthetic polymeric fibers made of poly-acids such as polylactic, polyglycolic or polyamino acids, polycaprolactone, absorbable epsilon caprolactone polymer, polypeptide gel, copolymers thereof and combinations thereof. The gel solution matrix can be a polymeric thermo-reversible gelling hydrogel. The support matrix is preferably biocompatible, biodegradable, hydrophilic, non-reactive, has a neutral charge and is able to have or has a defined structure.

In this application, "subchondral" means an area underlying joint cartilage. The term "subchondral bone" means a very dense, but thin layer of bone just below a zone of cartilage and above the cancellous or trabecular bone that forms the bulk of the bone structure of the limb. "Osteochondral" is a combined area of cartilage and bone where a lesion or lesions can occur. "Osteochondral defect" means a lesion, which is a composite lesion of cartilage and subchondral bone. "Hyaline cartilage" is cartilage consisting of groups of isogenous chondrocytes located within lacunae cavities, which are scattered throughout an extracellular collagen matrix. A "condyle" is a rounded articular surface of the extremity of a bone, Stedman's Medical Dictionary, 26$^{th}$ Ed., p 380 (1995); chondral means cartilaginous, Stedman's Medical Dictionary, 26$^{th}$ Ed., p 331 (1995); relating to or consisting of cartilage, Stedman's Medical Dictionary, 26$^{th}$ Ed., p 287 (1995). Osteochondral is bone and its associated cartilage.

Features of the invention will become apparent from the drawings and following detailed discussion, which by way of example without limitation describe preferred embodiments of the invention.

In the drawings, FIG. 1 is a schematic perspective view of a knee joint 10 (without patella), showing mating femur head 12 and tibia head 14. Femur head 12 includes femoral articular surfaces 16, femoral trochlear groove 18, femoral medial condyle 20 and femoral lateral condyle 22. FIG. 1 shows a trapezoid shaped harvested cavity 24 within femoral trochlear groove 18 representing a less strain area.

While FIG. 1 shows harvest from a trochlear groove 18, the osteochondral plug graft of the invention can be harvested from any appropriate structure including hyaline cartilage and underlying subchondral bone. Suitable harvest locations include weight bearing joints of mammals, including humans. These harvest locations include articular cartilage and rib cartilage. A wide variety of human articular cartilages can be used including cartilage from articulating surfaces of the knee, hip and shoulder joints. As specific examples, an osteochondral plug graft can be taken from the femoral condyle, the articulating surface of the knee and the articulating surface of the shoulder.

FIGS. 2 and 3 show harvested trapezoid shaped plug grafts 26 and multi cellular holding structure 40 representing embodiments of the invention. Trapezoidal graft 26 in FIG. 2 is harvested from the trochlear groove 18 shown in FIG. 1 to leave the harvested cavity 24. Trapezoid graft 26 is a quadrilateral having two parallel boundaries 28, 30 and four non parallel sloping sides 32. The graft 26 comprises an articular cartilage layer 34 and subchondral bone 36 harvested from the femoral trochlear groove 18 shown in FIG. 1.

Figure 7:
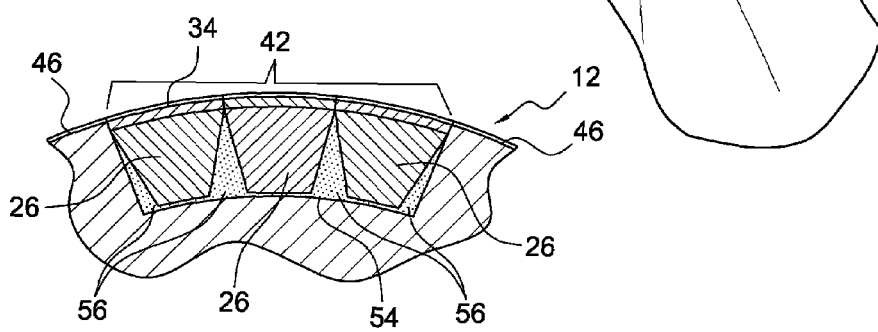
FIG. 7 is a schematic side elevation view of emplaced plug grafts.

In the FIG. 2 and FIG. 3 embodiments, trapezoid graft 26 is provided as an array 38 of grafts 26 in a multi cellular array structure 40. The Multi-cellular array structure 40 comprises a multiplicity of thin plastic-walled cells 44 suggestive of an egg crate. The cells 44 are separable. The separable feature can be an indent delineation of the cells 44. The separable feature allows a surgeon to select particular plug grafts 26 by separating cells 44 that include the selected grafts 26 from the rest of the array 40. The cells are separated by breaking off the selected cells, for example at applied indent delineations. The grafts can then be removed from the selected cells with the use of a hand tool or an adhesive surface, such as a tape. For example, a surgeon could select cells with a combination of a grid of 4×6 cm cells and a grid of 3×2 cm cells for implanting in a recipient socket requiring a combination of the 4×6 and 3×2 cells to complete a surface contour as shown in FIG. 7.

FIG. 2 shows a single graft 26 being emplaced in or removed from one cell 44 of array structure 40 and FIG. 3 shows an array 38 of grafts being emplace in or removed from the multiplicity of thin plastic-walled cells 44.

Figure 5:
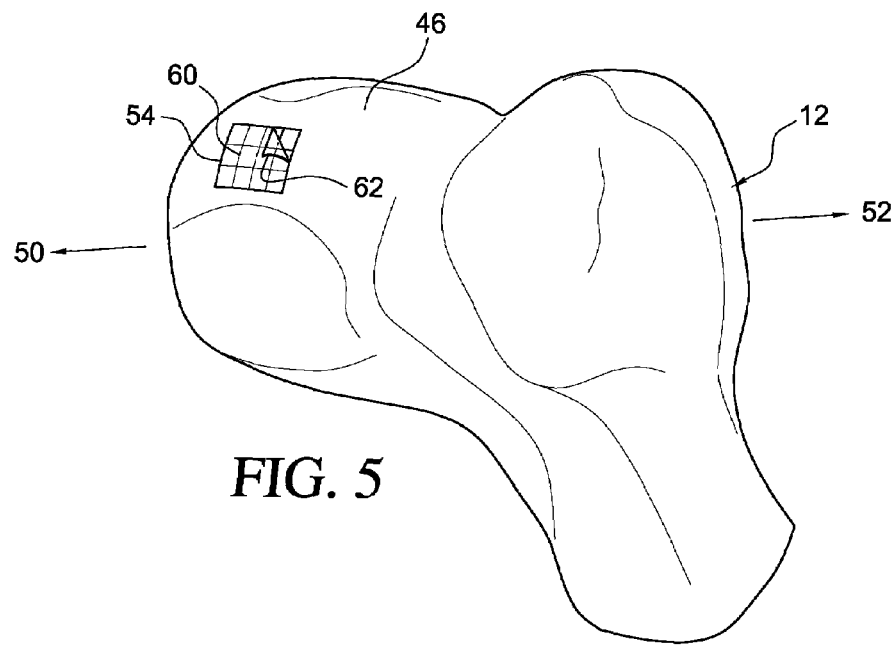
Figure 6:
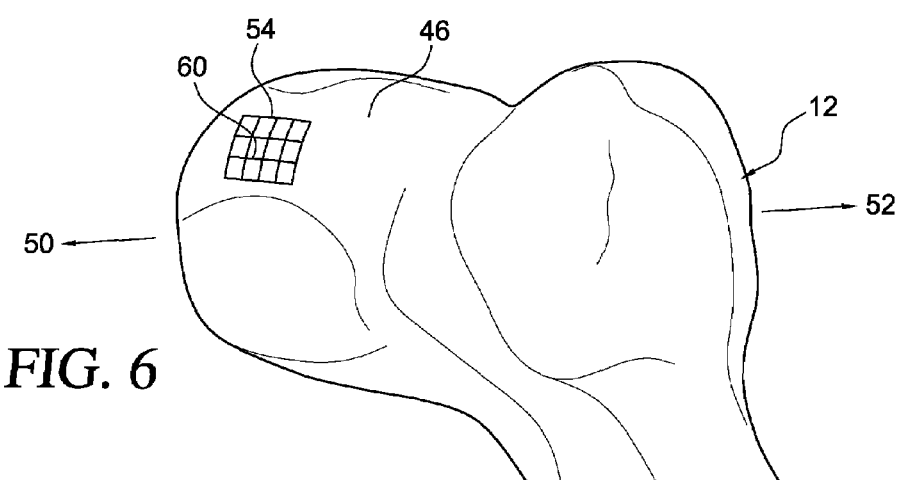

The plug grafts 26 of FIG. 2 and FIG. 3 are used to remedy an osteochondral defect, for example in an articular cartilage 46 of a femur head 12 as illustrated in FIGS. 4 through 6. FIGS. 4 through 6 show femur head 12 rotated 180° from the orientation shown in FIG. 1 so that lateral side 50 of the head 12 and medial side 52 of the head 12 are now reversed. Otherwise structure and numbering of the FIGS. 4 through 6 is the same as for femur head 12 of FIG. 1.

FIG. 4, shows a void formed by reaming around an osteochondral defect and removing the osteochondral defect from head 12 to leave routed recipient socket 54. In a process of repairing an osteochondral defect according to an embodiment of the invention, a defect is routed to form a recipient socket 54 in a trapezoid configuration to an exemplary depth of 4 to 6 mm.

In an embodiment, the array 38 of FIG. 2 and FIG. 3 is provided in different size multi-cellular array structures 40 so that a single or selected number of grafts 26 from cells 44 can be selected according to a requirement to fill a particular routed recipient socket 54. Hence, a single graft or multiple grafts of an array 38 can be selected to match the shape and extent of the socket 54. The graft 26 or multiple grafts 26 are separated from the array 38 and then ether separated from each other and emplaced within the socket 54 or placed as a contiguous unit of grafts in an arrangement that matches the extent and size of the recipient socket 54. FIG. 4 shows a mosaic 60 of selected grafts 36 being emplaced to fill routed recipient socket 54.

In an embodiment, the grafts are retained in the cells 44 and emplaced into the recipient socket 54 as a unit held together by the cell structure of the multi-cellular array structure 40. In this embodiment, the multi-cellular array structure 40 serves to position the grafts 26 when a plurality of grafts 26 are emplaced within a socket 54 and also serves to protect articular surfaces of the individual grafts 26 during shipping and graft positioning.

Referring back to FIGS. 2, 3 and 4, a graft 26 is provided within the array structure 40 with articular cartilage layer 34 facing upward so that a tape 62 can be applied to the exposed graft surface 34 to remove a single graft 26 or multiple grafts 26 from the array structure 40 for application to the socket 54. Then as shown in FIGS. 5 and 6, the tape 62 can be removed after positioning of the graft 26 or grafts 26 within the socket 54.

The tape 62 is one preferred embodiment to transport plug grafts 26 to a recipient socket 54. A tape permits easy transfer of otherwise difficult to handle delicate grafts. The tape retains a tight fit between implanted grafts if the grafts are picked from a tight packed arrangement. A tape 62 facilitates easy removal of an implanted graft 26 from a socket 54 in an instance where repositioning of the graft or replacement of a misfit graft is required. In an embodiment, the tape 62 is flexible so as to retain an original surface contour of a plurality of plug grafts. This feature can be used for an implant to maintain a mimic of a surface contour of a donor site. In another embodiment, the tape 62 is biodegradable. In this instance, it can be left in place to retain a contour until degraded away. While in place, the tape 62 provides added support and protection to an implanted plug graft 26 or particularly to a plurality of grafts. The emplaced tape provides a physical barrier to inflow of synovial fluid and acts to retain exuded blood, cells and other beneficial components of the implant. In an embodiment, the tape 62 can contain a growth factor to enhance cartilage integration with surrounding graft 26 and host bone.

The tape embodiment can be of particular advantage in the instance that the multi-cellular array structure contains trapezoid shaped grafts as in FIGS. 2 and 3. For one reason, corner angles of the trapezoidal shape act to limit individual graft 26 rotation around a vertical axis within the socket 54.

A plurality of plug grafts 26 can be used to provide an advantageous graft assembly 42 of the invention, configured for receipt within a single surgically prepared recipient socket 54 as shown in FIG. 7. The plug grafts 26 in a plurality within recipient socket 54 can provide a mechanical arch that mimics a contour of an adjacent host chondral area. FIG. 7 shows the plurality of trapezoid grafts 26 packed to form an arch within a socket 54 to provide articular cartilage layer 34 surface that is even with adjacent articular cartilage surface 64 of a surrounding femoral articular surface 16. The FIG. 7 shows a plurality of grafts 26 oriented side to side to form the articular surface contour dome to complete adjacent articular cartilage surface 64.

Figure 8:
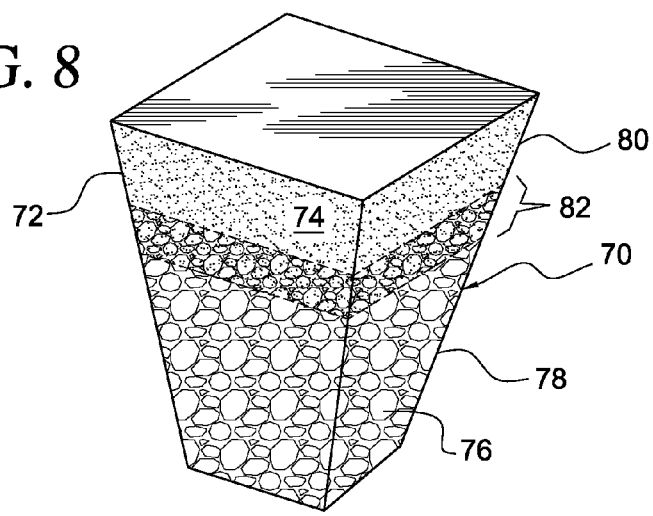
FIG. 8 is a schematic perspective view of a trapezoid shaped biologic structure.

FIG. 8 illustrates another preferred embodiment of the invention. In the FIG. 8 embodiment, a trapezoid shaped bio-resorbable repair assembly 70 is adapted to regenerate damaged or destroyed articular cartilage on the surface of a bone by establishing a chondrogenic growth-supporting matrix between an area of damaged or destroyed articular cartilage that has been removed and an adjacent healthy area of articular cartilage and cancellous bone.

In this embodiment, the repair assembly 70 includes a trapezoid configured resorbable osteoconductive matrix 72 dimensioned to be inserted in routed recipient socket 54 to establish communication with adjacent healthy tissue. The trapezoid shaped repair assembly 70 comprises a resorbable osteoconductive matrix 72, a biological agent 74 such as bone morphogenetic protein (BMP) and cultured chondrogenic cells 76. The resorbable osteoconductive matrix 72 is a spongelike matrix body having the biological agent 74 absorbed in a lower portion 78, dispersed cells 76 in the upper portion 80 and a intermediate transition zone 82.

The trapezoid shaped biological repair assembly 70 can be implanted similarly to placement of a harvested graft 24 to fill a recipient socket 54. Once implanted, the trapezoidal shaped biological repair assembly 70 fills the socket 54 by simulating cartilage and bone growth.

The resorbable osteoconductive matrix 72, biological agent 74 and cells 76 are described in detail as follows:

Resorable Osteoconductive Matrix (ACS)

While type I collagen is a preferred source for the inventive resorbable osteoconductive matrix 74 due to its availability, ease of isolation and purification, and biocompatible properties, other fibril forming collagen such as types II, III, V and XI and physiologically compatible collagen obtained from transgenic animals may be used either singularly or in combination with type I collagen. The primary source of type I collagen is tendon, skin, bone, and ligament. Human or animal tissues may be used to isolate the collagen. In general, animal tissues are preferred due to easy availability in fresh forms from local slaughter houses. Other possible matrix materials include hyaluronan, alginate, chitosan and the like.

Advantageously, animal type I collagen is homologous to human type I collagen. Therefore, medical devices prepared from animal-derived (e.g., bovine, porcine, ovine, equine) type I collagen are accepted for human implantation. Type I collagen-based grafts can enhance wound healing during tissue and organ regeneration. Type I collagen fibers can be engineered into a variety of types of matrices. Cells and bioactive agents (drugs, growth factors, genes) can be incorporated for enhanced function. A final advantage is that Type I collagen-based products can be cost effectively manufactured in large quantities.

In a preferred embodiment, the osteoconductive matrix is purified from Type I bovine tendon collagen in the form of an absorbable collagen sponge (ACS). The purified type I collagen ACS material can be engineered into a variety of extracellular tissue matrices having specific characteristics to be used either alone or in combination with cells and bioactive molecules for tissue and organ regeneration applications.

ACS is derived from the Achilles tendon of steers at the beginning of beef production. The tendon is harvested in the United States from USDA-cleared food-grade herds. The tendon tissue is virtually avascular and is the first tissue to be harvested, which reduces the risk of infection or contamination. After harvesting, the tendon is treated with alkali solutions to become the sponge like material that is particularly suitable as the resorbable osteoconductive matrix of the invention. After the collagen is formed into a sponge, the material is sterilized with ethylene oxide.

ACS is available as an absorbable hemostatic agent, Helistat® agent from Integra Life Sciences, Plainsboro, N.J.). Once implanted, the ACS osteoconductive matrix undergoes resorbtion over a 4- to 12-week period via cell-mediated degradation by macrophages. The collagen can provide a favorable surface for cell attachment during early osteoid formation. It then undergoes resorbtion. ACS osteoconductive matrix possesses all the properties of an ideal carrier for many biological agents and is particularly suited for BMP.

The resorbable osteoconductive matrix 72 has pores of a sufficient size and quantity to permit growing tissue to infiltrate therein. The pore size preferably ranges from about 10 μm to about 500 μm, more preferably from about 50 μm to about 150 μm with surface pores being smaller than cross-sectional (internal) pores. In particularly preferred embodiments, the surface pores range in diameter from about 30 μm to about 150 μm, with about 70 μm being most preferred. Cross-sectional pores can range in diameter from about 50 μm to about 300 μm, with about 150 μm being most preferred.

Biological Agent

The resorbable osteoconductive matrix can include a supported interposed biological agent such as a regenerative material. The term "biological agent" defines an entity that is added to the osteoconductive matrix to effect a therapeutic end, such as facilitation of bone growth, prevention of disease, administration of pain relief chemicals, administration of drugs, and the like. Examples of biological agents include antibiotics, growth factors, fibrin, bone morphogenetic factors including bone morphogenetic protein (BMP), transforming growth factor b (TGF-b), growth differentiation factor (GDF), cartilage derived morphogenetic protein (CDMP) bone growth agents, anti-inflammatory agents, chemotherapeutics, pain killers, bisphosphonates, strontium salt, fluoride salt, magnesium salt and sodium salt.

Preferred biological agents 74 include bone morphogenetic proteins (BMPs) that belong to the transforming growth factor-{3 (TGF.(3) superfamily of structurally related signaling proteins. They initiate, promote and regulate bone development, growth, remodeling and repair. In addition to bone and cartilage morphogenesis, BMP is involved in prenatal development and postnatal growth of eye, heart, lung, kidney, skin and other tissues. Many BMPs have osteoinductive capability since they induce mesenchymal stem cells into osteoblasts, the cells that form new bone. Studies have demonstrated the efficacy of some BMPs in bone repair. Specific to the spine, studies have shown comparable or improved spine fusion rates with use of BMP in a carrier versus use of an autograft.

Cultured Chondrogenic Cells

The repair assembly 70 can include cells attached to the biocompatible support matrix. The cells can be chondroprogenitor cells or otherwise. The cells can be autologous, allogenic or xenogenic in origin. In the present method, an osteochondral graft is produced in vitro by culturing isolated chondroprogenitor cells 76 for an amount of time effective for the formation of a chondrogenic cell-associated matrix. The chondroprogenitor cells 76 with cell-associated matrix are previously cultured on a porous biocompatible support scaffold in the presence of a growth factor, for a time effective for allowing both the formation of an engineered cartilage tissue and attachment of the engineered cartilage tissue to the biocompatible support scaffold.

Another known option to treat damaged articular cartilage is a cartilage transplant, referred to as a Mosaicplasty or osteoarticular transfer system (OATS) technique. This technique involves using a series of dowel cutting instruments to harvest a plug of articular cartilage and subchondral bone from a donor site, which can then be implanted into a core made into the defect site. By repeating this process, transferring a series of plugs, and by placing them in close proximity to one another, in mosaic-like fashion, a new grafted hyaline cartilage surface can be established. The result is a hyaline-like surface interposed with a fibrocartilage healing response between each graft.

Such an OATS procedure is technically difficult, as all grafts must be taken with the axis of the harvesting coring drill being kept perpendicular to the articular surface at the point of harvest. Also, all graft placement sites must be drilled with the axis of a similar coring tool being kept perpendicular to the articular surface at the point of implantation. Further, all grafts must be placed so that the articular surface portion of these cartilage and bone plugs is delivered to the implantation site and seated at the same level as the surrounding articular surface. If these plugs are not properly placed in relation to the surrounding articular surface, the procedure can have a very detrimental effect on the mating articular surface. If the plugs are placed too far below the level of the surrounding articular surface, no benefit from the procedure will be gained. Further, based on the requirement of perpendicularity on all harvesting and placement sites, the procedure requires many access and approach angles that typically require an open field surgical procedure. Finally, this procedure requires a lengthy post-operative non-weight bearing course.

Transplantation of previously harvested hyaline cartilage cells from the same patient has been utilized in recent years. After the cartilage is removed or harvested, it is cultured in the lab to obtain an increase in the number of cells. These cells are later injected back into the focal defect site and retained by sewing a patch of periosteal tissue over the top of the defect to contain the cells while they heal and mature. The disadvantages of this procedure are its enormous expense, technical complexity, and the need for an open knee surgery. Further, this technique is still considered somewhat experimental and long-term results are unknown. Some early studies have concluded that this approach offers no significant improvement in outcomes over traditional abrasion and microfracture techniques.

Procedure

In an exemplary procedure according to the invention, osteochondral plug grafts can be harvested from a lower weight-bearing donor area in the same transplant joint as a target defect surface. In a preferred embodiment, the plug graft is a preserved allograft tissue plug. The harvest procedure can be performed as an arthroscopic or open surgery. Factors that can be considered in identification of a donor site include site morbidity, effects of joint incongruity on the opposing surface of the donor site, damage to the chondrocytes at articular margins of the donor and recipient sites during preparation and implantation, and collapse or settling of a selected graft over time. In an example, an osteochondral plug graft comprising a subchondral bone base and overlying cartilage cap is harvested from an inner rim of a intercondylar notch with a trephine. The plug is then chiseled to a trapezoid shape with either two only parallel sides or two pairs of parallel sides. The plug can be shaped with the chisel in various dimensions depending on the size and configuration of the defect being treated. Then, the plug graft can be treated to remove cellular debris and proteoglycans.

The diameter or diagonal of the plug can range from 1 mm to 30 mm but is preferably 3 mm to 10 mm, which is small enough to fit through an endoscopic cannula, but large enough to minimize the number of plugs needed to fill a large recipient socket. The size is selected to provide good results within a recipient socket and to provide a confluent hyaline surface as describe with reference to FIGS. 4 through 7. The thickness of subchondral bone can be modified to match anatomy of the recipient site so that the surface cartilage of the plug or plugs will be even with and follow the surface cartilage of the recipient tissue as shown in FIG. 7. The plug can be inserted arthroscopically similarly to a mosaicplasty procedure or through an open incision. In one aspect, the plug or plugs are inserted manually with the aide of an adhesive strip such as a tape as described with reference to FIGS. 4 through 6. The tape is used to select a plurality of plug grafts from the FIG. 3 array 38 and to permit implantation into the open recipient socket as a mosaic unit 60 as shown in FIG. 4.

In an exemplary procedure, a recipient socket 54 is formed in a defect. An exemplary technique for forming the socket is to drill a hole in femur 12 to a depth substantially corresponding to the height of the proposed plug graft. The socket can have similar dimensions to a plug graft for secure fit of a single graft into a socket or can have complementary configuration and size to a plurality of plug grafts for multiple insertion as shown in FIG. 6 and FIG. 7.

A small amount of biologic glue can be smeared into the socket and the plug inserted into the glue lined socket. Suitable organic glues include TISSEEL® or TISSUCOL® (fibrin based adhesive; Immuno AG, Austria), Adhesive Protein (Sigma Chemical, USA), Dow Corning Medical Adhesive B (Dow Corning, USA), fibrinogen thrombin, elastin, collagen, alginate, demineralized bone matrix, casein, albumin, keratin and the like. A composite fibrin glue can be mixed with milled cartilage from for example, a bovine fibrinogen (e.g., SIGMA F-8630), thrombin (e.g., SIGMA T-4648) and aprotinin (e.g., SIGMA A6012). Also, human derived fibrinogen, thrombin and aprotinin can be used.

The fibrin glue can be mixed with milled or minced cartilage and can be injected into the defect after the plug or plugs are inserted or can be smeared into socket 54 before insertion of the plug(s). The fibrin glue fills the gap or space 56 between plugs and the socket walls as shown in FIG. 6. The plug or plugs are moveable in the defect socket 54 until the fibrin glue can be polymerized (set). The FIG. 6 shows a larger recipient socket 54 requiring more than one plug with the fibrin glue filling spaces 56 among the plugs 26. In an embodiment of the invention, the glue can include an anabolic factor such as BMP, GDF, CDMP or progenitor cells.

The plug graft 26 can be inserted into the glue containing socket 54 by hand using a tape or using any suitable instrument. The plug graft is placed or forced, in an axial direction into the socket 54 with the outer surface 34 of the trapezoid plug graft 26 engaging inner surface of articular cartilage 46 of inner walls of the socket 54 or engaging surfaces 34 of adjacent plug grafts 26 as shown in FIG. 7. The plug graft(s) 26 is positioned so that its surface is flush with the surface of the surrounding cartilage area.

Figure 9:
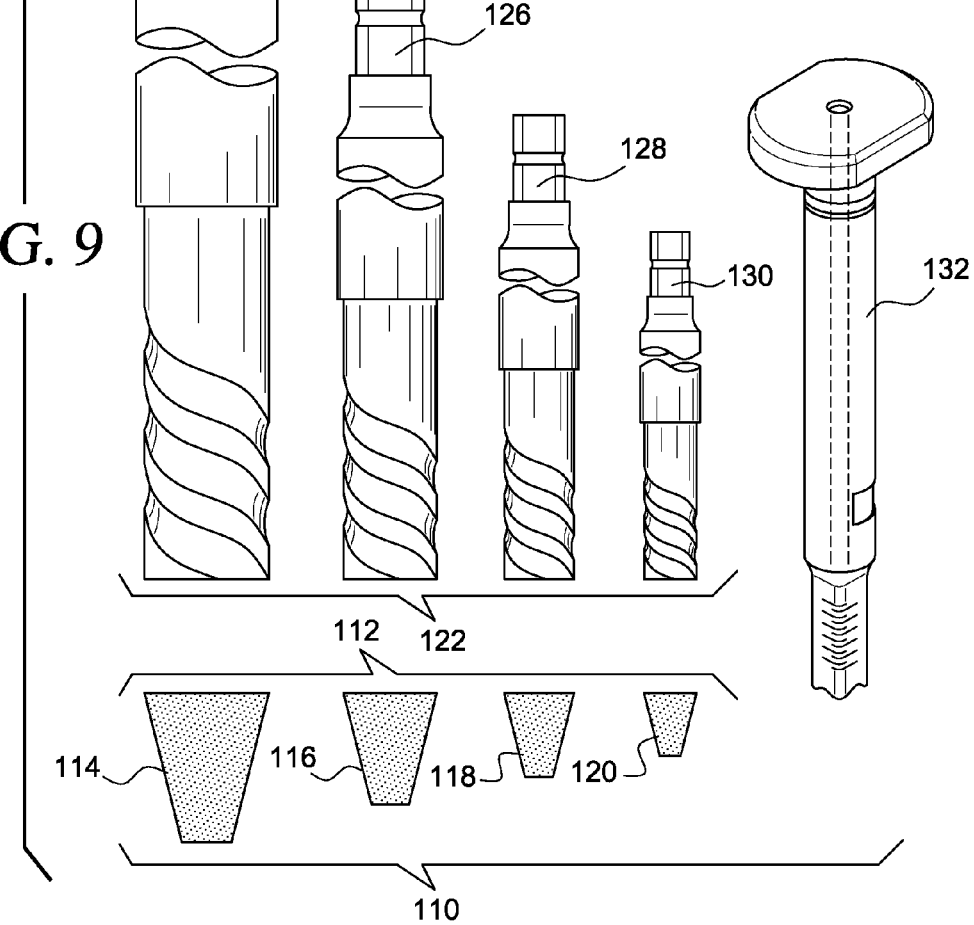
FIG. 9 is a schematic representation of a kit of parts to carry out osteochondral regeneration procedures.

The trapezoid shaped implant can be provided to a surgeon as part of a kit of implants. FIG. 9 illustrates a kit of parts to carry out an osteochondral regeneration procedure according to the invention. FIG. 9 shows kit 110 comprising an array 112 of trapezoid shaped plug grafts. The array 112 includes exemplary 8 mm plug 114, 6 mm plug 116, 4 mm plug 118 and 2 mm plug 120. The array 112 is provided to a surgeon to select an appropriate size and configuration according to the size and configuration of a recipient socket. Additionally, the kit 110 includes a plurality 122 of custom drill heads 124, 126, 128 and 130 to form a plurality of sized recipient sockets in an osteochondral area and a chisel 132 to provide a final shape to a drilled recipient socket.

While preferred embodiments of the invention have been described, the present invention is capable of variation and modification and therefore should not be limited to the precise details of the drawing examples. The invention includes changes and alterations that fall within the purview of the following claims.

What is claimed is:

1. A method for repairing articular cartilage in a patient, comprising:

harvesting a plurality of cartilage surfaced and lower subchondral bone portioned trapezoid shaped plug grafts from a chondral area;

forming the plug grafts into a plurality of trapezoid shapes having a bottom surface substantially parallel to the articular cartilage top surface wherein the lower subchondral bone sides are tapered from the articular cartilage top surface;

providing the plurality of trapezoid shaped plug grafts in an array for graft selection;

forming a recipient socket in a chondral area of an articular surface in need of repair;

selecting one or more plug grafts from the array by applying an adhesive tape to a surface of one or more grafts to be selected; and implanting the one more trapezoid shaped plug grafts into the recipient socket for osteochondral repair of the area.

2. The method of claim 1, comprising harvesting a plug graft from another chondral area; and forming the plug graft into a trapezoid shape for implanting; and implanting the plug graft as a part of a tight packed array of plug grafts within the routed recipient socket in the articular surface in need of repair.

3. The method of claim 1, comprising: forming the recipient socket in the chondral area; applying a glue into the socket; and implanting the at least one or more trapezoid shaped grafts into the glue containing recipient socket.

4. The method of claim 3, wherein the glue comprises an anabolic factor selected from BMP, TGF-b, GDF, CDMP and progenitor cells.

5. The method of claim 1, wherein at least one of the trapezoid shaped plug grafts is a quadrilateral shape comprising an articular cartilage top surface with a lower subchondral bone portion having two parallel sides and a bottom subchondral surface.

6. The method of claim 1, wherein the adhesive tape is biodegradable; and the method further comprises retaining an implanted one or more grafts with the adhesive tape in the recipient socket.

7. The method of claim 1, wherein the adhesive tape is biodegradable and comprises an anabolic growth factor selected from BMP, TGF-b, GDF, CDMP and progenitor cells; and the method further comprises retaining an implanted one or more grafts with the adhesive tape in the recipient socket.

* * * * *